(12) United States Patent
Riggs et al.

(10) Patent No.: US 9,232,785 B2
(45) Date of Patent: Jan. 12, 2016

(54) METHOD FOR REDUCING SUNBURN DAMAGE IN PLANTS

(75) Inventors: Richard Riggs, Mannheim (DE); Dieter Strobel, Herxheim am Berg (DE); Jochen Prochnow, Neustadt (DE); Pilar Puente, Speyer (DE); Petra Volz, Neustadt (DE)

(73) Assignee: BASF SE, Ludwigshafen (DE)

( * ) Notice: Subject to any disclaimer, the term of this patent is extended or adjusted under 35 U.S.C. 154(b) by 9 days.

(21) Appl. No.: 13/262,362

(22) PCT Filed: Mar. 25, 2010

(86) PCT No.: PCT/EP2010/053902
§ 371 (c)(1),
(2), (4) Date: Sep. 30, 2011

(87) PCT Pub. No.: WO2010/115721
PCT Pub. Date: Oct. 14, 2010

(65) Prior Publication Data
US 2012/0017503 A1    Jan. 26, 2012

(30) Foreign Application Priority Data
Apr. 2, 2009 (EP) ................... 09157179

(51) Int. Cl.
| A23B 7/14 | (2006.01) |
| A01N 3/00 | (2006.01) |
| A01N 37/34 | (2006.01) |
| A01N 43/647 | (2006.01) |
| A01N 43/653 | (2006.01) |
| A01N 43/84 | (2006.01) |

(52) U.S. Cl.
CPC *A01N 3/00* (2013.01); *A01N 37/34* (2013.01); *A01N 43/647* (2013.01); *A01N 43/653* (2013.01); *A01N 43/84* (2013.01)

(58) Field of Classification Search
CPC ..... A01N 43/84; A01N 43/653; A01N 47/24; A01N 3/00
USPC ............................................. 47/57.7; 514/203
See application file for complete search history.

(56) References Cited

U.S. PATENT DOCUMENTS

| 6,884,798 B2 * | 4/2005 | Baron et al. ................... 424/761 |
| 2008/0306026 A1 * | 12/2008 | Shirley et al. ................... 514/89 |

FOREIGN PATENT DOCUMENTS

| CA | 1 195 246 | 10/1985 |
| EP | 0 083 308 | 7/1983 |
| GB | 1 552 277 | 9/1979 |
| WO | WO 2007/110801 | 10/2007 |
| WO | WO 2008/085682 | 7/2008 |
| WO | WO2009/153231 A2 * | 6/2009 | ............. A01N 25/26 |

OTHER PUBLICATIONS

Gabriele et al., Protection of Mildewcides and Fungicides from Ultraviolet Light Induced Photo-Oxidation, Journal of Coatings Technology, vol. 56, No. 712, pp. 33-48, May 1, 1984, Search Report.
Burchard et al., "Contribution of hydroxycinnamates and flavonoids to epidermal shielding of UV-A and UV-B radiation in developing rye primary leaves as assessed by ultraviolet-induced chlorophyll fluorescence measurements", Plant, Cell and Environment, vol. 23, No. 12, pp. 1373-1380, Dec. 1, 2000, Search Report.
International Search Report, PCT/EP2010/053902, Mar. 23, 2011.
International Preliminary Report on Patentability, PCT/EP2010/053902, Aug. 8, 2011.

* cited by examiner

*Primary Examiner* — Johann R Richter
*Assistant Examiner* — Yanzhi Zhang
(74) *Attorney, Agent, or Firm* — Brinks Gilson & Lione

(57) ABSTRACT

The present invention relates to methods, use and compositions for reducing sunburn damage in plants. More specifically, it relates to methods and compositions for controlling, preventing, or treating sunburn damage using UV filters.

7 Claims, No Drawings

METHOD FOR REDUCING SUNBURN DAMAGE IN PLANTS

This application is a National Stage application of International Application No. PCT/EP2010/053902 filed Mar. 25, 2010, the entire contents of which is hereby incorporated herein by reference. This application also claims priority under 35 U.S.C. §119 to EP Patent Application No. 09157179.4, filed Apr. 2, 2009, the entire contents of which is hereby incorporated herein by reference.

The present invention relates to methods, use and compositions for reducing sunburn damage in plants. More specifically, it relates to methods and compositions using organic UV filters for reducing sunburn damage.

Sunburn is not limited to animals. Sunburn is a significant and common cause of damage to trees and plants. Plant-related sunburn, also called sun-scorching, also involves damage to tissue, caused by light, and in particular the UV-radiation stemming from the sun.

Crop plants, e.g. pineapple plants and fruits are susceptible to damage from solar radiation and high temperatures. Damage to pineapples can result in significant financial losses. Symptoms include external sunburn or bleaching and internal sunburn or "boiling". Pineapples with external sunburn show a bleached, yellow-white skin that turns pale grey/brown upon damage to the tissue underneath. These damaged areas are susceptible to disease infection. Sunburn is common during hot (>32° C.), periods of the year. Internal sunburn, thought to be the result of high air temperatures, renders the fruit unfit for commercial use. Internal sunburn cannot be detected without cutting open the fruit. Highly translucent fruits appear to be most susceptible to internal sunburn.

The chances of getting sunburn damage increase as air temperatures reach 30° C. and above. In Australia, some commercial producers report losses of over 20 percent of yield to sunburn damage—with even greater losses in times of extreme heat- and that may not count unmarketable produce left unpicked.

Sunburn damage is also known to occur in cereals such as barley where abiotic leaf spots (also known as Physiological Leaf Spots (PLS); or Non-parasitic leaf spots (NPLS)) can cause extensive damage to the upper leaves in spring and winter barley once crops are past the flowering stage of growth. This can cause extensive losses in yield and quality. These sunburn damage symptoms of barley cultivars *Hordeum vulgare* L. are a leaf damage which has been observed only in the last fifteen years. It is observed that they mostly occur when the radiation is high and the plants are in a defined stage of development.

The use of metal oxide UV absorbers such as titanium dioxide in the agrochemistry is known: WO 2007/014826 discloses the use of a preparation containing a UV radiation absorbing metal oxide powder for the reduction of sunburn damage to useful plants. EP 1 139 763 B1 discloses the use of a particulate material such as titanium dioxide to reduce physiological disorders of a plant without diminishing photosynthesis.

Although a positive effect of titanium dioxide on plants was described, a severe disadvantage of titanium dioxide is known: Topalov et al., Water Research 1999, 33, 1371-1376 disclose the photocatalytic activity of titanium dioxide towards the decomposition of the fungicide metalaxyl. Kuer and Nunez, Pest Management Science, 2007, 63, 491-494, disclose the degradation of nitrogen heterocycles, the basic structural units of a large number of commercial herbicides and fungicides, using titanium dioxide as photocatalyst. In the abstract of JP2004323501, titanium dioxide is disclosed as photocatalyst for decomposing residual agrochemicals used for the agricultural products. Due to the fact that metal oxide UV filters are not oil- or water-soluble, metal oxide UV filters require the addition of superspreading agents to form a desirable uniform and transparent coveraging of the plant parts to be protected against sunburn damage.

One typical problem arising in the field of sunburn control lies in the need to reduce the dosage rates of the UV filters in order to reduce or avoid unfavorable environmental or toxicological effects whilst still allowing reduction of sunburn damage. Another problem encoutered concerns the need to have available UV filters which show an improved action against sunburn with a reduced amount of active compounds applied.

It was therefore an object of the present invention to provide uses and methods which solve the problems outlined above. This object is in part or in whole achieved by the uses, methods and compositions defined below.

Accordingly, the present invention relates to the use of at least one UV filter chosen from the following groups:

A) benzotriazoles, such as 2-(2H-benzotriazol-2-yl)-4,6-bis(1-methyl-1-phenylethyl)-phenol (Tinuvin® 900, CIBA AG), [3-[3-(2H-benzotriazol-2-yl)-5-(1,1-dimethylethyl)-4-hydroxyphenyl]-1-oxopropyl]-w-[3-[3-(2H benzotriazol-2-yl)-5-(1,1-dimethylethyl)-4-hydroxyphenyl]-1-oxopropoxy]poly(oxy-1,2-ethanediyl) (Tinuvin® 1130, CIBA AG), 6-tert.-butyl-2-(5-chloro-2H-benzotriazol-2-yl)-4-methylphenol, 2,4-ditert-butyl-6-(5-chloro-2H-benzotriazol-2-yl)-phenol, 2-(2H-benzotriazol-2-yl)-4,6-di-tert.-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl)phenol, compounds of formula I

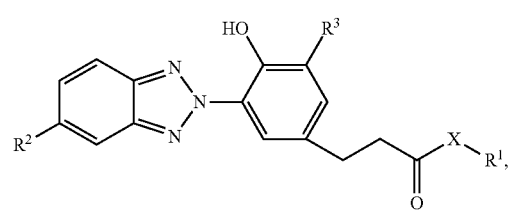

wherein
X is NH or O;
R¹ is [C₂-C₄-alkoxy]ₙ-(C₁-C₁₈-alkyl) or —[CH₂CH₂NH], —H;
R² is H or Cl;
R³ is H or C₁-C₈-alkyl; and
n is an integer between 3 and 50;

B) Cyanoacrylate derivatives, such as ethyl 2-cyano-3-phenylcinnamate (Uvinul® 3035, BASF SE), 2-cyano-3,3-diphenylacrylic acid-2'-ethylhexyl ester or 2-ethylhexyl 2-cyano-3-phenylcinnamate (octocrylene, Uvinul® 539 T, Uvinul 3039, BASF SE), compounds of formula

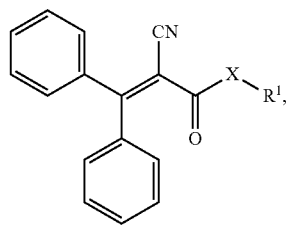

wherein
X is NH or O;
R¹ is [C₂-C₄-alkoxy]n-(C₁-C₁₈-alkyl) or —[CH₂CH₂NH], —H;

$R^2$ is H or Cl; and
n is an integer between 3 and 50;

C) para-aminobenzoic acid (PABA) derivatives, especially esters, such as ethyl-PABA, ethoxylated PABA, ethyldihydroxypropyl-PABA, Glycerol-PABA, 2-ethylhexyl 4-(dimethylamino)benzoate (Uvinul® MC 80), 2-octyl 4-(dimethylamino)benzoate, amyl 4-(dimethylamino) benzoate, 4-bis(polyethoxy)-4-amino benzoic acid polyethoxyethyl ester (Uvinul® P 25, BASF SE);

D) esters of salicylic acid, such as 2-ethylhexyl salicylate, 4-isopropylbenzyl salicylate, homomethyl salicylate, TEA salicylate (Neo Heliopan® TS, Haarmann and Reimer), dipropyleneglycol salicylate;

E) esters of cinnamic acid, such as 2-ethylhexyl 4-methoxycinnamate (Uvinul® MC 80), octyl-p-methoxycinnamate, propyl 4-methoxycinnamate, isoamyl 4-methoxycinnamate, conoxate, diisopropyl methylcinnamate, etocrylene (Uvinul® N 35, BASF SE), compounds of furthermore compounds of formula

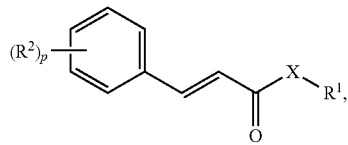

wherein
X is NH or O;
$R^1$ is H or $[C_2\text{-}C_4\text{-alkoxy}]n\text{-}(C_1\text{-}C_{18}\text{-alkyl})$ or $—[CH_2CH_2NH]_n—H$;
$R^2$ is OH or $C_1\text{-}C_8$-alkoxy;
p is an integer between 0 and 5; and
n is an integer between 3 and 50;

F) derivatives of benzophenone, such as 2-hydroxy-4-methoxybenzophenone (Uvinul® M 40, BASF SE), 2-hydroxy-4-methoxy-4'-methylbenzophenone, 2,2'-dihydroxy-4-methoxybenzophenone, 2-(4-diethylamino-2-hydroxybenzoyl)-benzoic acid hexylester (Uvinul® A Plus, BASF SE), 4-n-octyloxy-2-hydroxybenzophenone (Uvinul® 3008, BASF SE), 2-hydroxybenophenone derivatives such as 4-hydroxy-, 4-methoxy-, 4-octyloxy-, 4-decyloxy-, 4-dodecyloxy-, 4-benzyloxy-, 4,2',4'-trihydroxy-, 2'-hydroxy-4,4'-dimethoxy-2-hydroxybenzophenone;), compounds of formula:

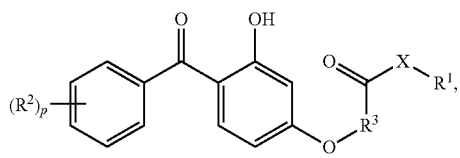

wherein
X is NH or O;
$R^1$ is H or $[C_2\text{-}C_4\text{-alkoxy}]n\text{-}(C_1\text{-}C_{18}\text{-alkyl})$ or $—[CH_2CH_2NH]_n—H$;
$R^2$ is OH or $C_1\text{-}C_8$-alkoxy;
p is an integer between 0 and 5; and
$R^3$ is H or $C_1\text{-}C_8$-alkyl; and
n is an integer between 3 and 50;

G) sulfonic acid derivatives of benzophenones, such as 2-hydroxy-4-methoxybenzophenone-5-sulfonic acid (Uvinul® MS 40, BASF SE) and its salts, 2,2'-dihydroxy-4,4#-dimethoxybenzophenone-5,5'-sulfonic acid and its salts (disodium salt: Uvinul® DS 49, BASF SE);

H) 3-benzylidenecamphor and derivatives thereof, such as 3-(4'-methylbenzylidene)d-1-camphor, benzylidiene camphor sulfonic acid (Mexoryl® SO, Chimex);

I) sulfonic acid derivatives of 3-benzylidenecamphor, such as 4-(2-oxo-3-bornylidenemethyl)benzenesulfonic acid and 2-methyl-5-(2-oxo-3-bornylidene)sulfonic acid and salts thereof;

J) esters of benzalmalonic acid, such as 2-ethylhexyl 4-methoxybenzmalonate;

K) triazine derivatives, such as dioctylbutamidotriazone (Uvasorb® HEB, Sigma), 2,4,6-trinanilino-p-(carbo-2'-ethyl-hexyl-1'-oxy)-1,3,5-triazine (Uvinul® T 150, BASF SE), 2-[4-[(2-Hydroxy-3-(2'-ethyl)hexyl)oxy]-2-hydroxyphenyl]-4,6bis-(2,4-dimethylphenyl)-1,3,5-triazine (Tinuvin® 405, CIBA AG), anisotriazine (Tinosorb® S, CIBA AG), 2,4,6-tris(diisobutyl 4'-aminobenzalmalonate)-s-triazine, compounds of formula:

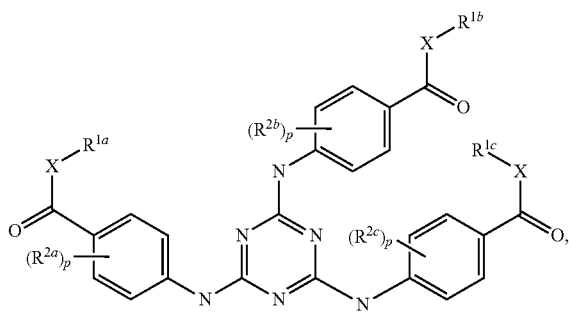

wherein
X is NH or O;
$R^{1a}, R^{1b}, R^{1c}$ are independently of each other H, $[C_2\text{-}C_4\text{-alkoxy}]_n\text{-}(C_1\text{-}C_{18}\text{-alkyl})$ or $—[CH_2CH_2NH]_n—H$;
$R^{2a}, R^{2b}, R^{2c}$ are independently of each other OH or $C_1\text{-}C_8$-alkoxy;
p is an integer between 0 and 4; and
n is an integer between 3 and 50;

L) Propane-1,3-diones, such as, 1-(4-tert-butylphenyl)-3-(4'-methoxyphenyl)propane-1,3-dione;

M) 2-phenylbenzimidazole-5-sulfonic acid or 2-phenylbenzimidazole-4-sulfonic acid and alkali metal, alkaline earth metal, ammonium, alkylammonium, alkanolammonium and glucammonium salts thereof;

N) derivatives of benzoylmethane, such as, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione;

O) Aminohydroxy-substituted derivatives of benzophenones, such as N,N-diethyl-aminohydroxybenzoyl-n-hexylbenzoate; and P) mixtures of UV filters of groups A) to N), such as a mixture of p-methoxycinnamic acid ethylhexyl ester (65%) and 2-(4-diethylamino-2-hydroxybenzoyl)benzoic acid hexylester (35%) (Uvinul® A Plus B, BASF SE);

for reducing sunburn damage in plants.

The UV filters of groups A) to P) are known and are used in cosmetics, such as sunscreen, lipsticks or for stabilization of polymers such as plastics. Many of them are commercially available (such as Uvinul® products (BASF SE) or Tinuvin® products (CIBA AG) or may be found in EP 0 280 650; U.S. 61/160,124. UV filters encompass compounds of the following classes: benzophenones, benzotriazoles, cyanoacrylates, cinnamic acid esters, para-aminobenzoates (PABA), naphthalimides, hydroxyphenyltriazines and oxalanilides.

EP 0 280 650 discloses benzotriazoles of formula

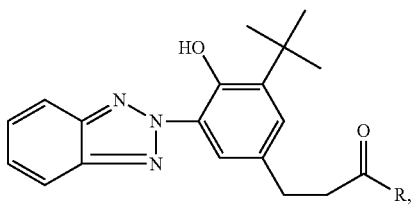

wherein R is e.g. —OCH$_2$CH$_2$OCH$_2$CH$_2$OC$_2$H$_5$ or —NHCH$_2$CH$_2$OC$_2$H$_5$.

Tinuvin® 384-2: a commercially available UV filter (CIBA AG) from the class of benzotriazoles (95% benzenepropionic acid, 3-(2H-benzotriazol-2-yl)-5-(1,1-dimethylethyl)-4-hydroxy-, C$_{7-9}$-alkyl ester and 5% 1-methoxy-2-propylacetate).

Tinuvin® 109: a commercially available UV filter (CIBA AG) from the class of benzotriazoles (mixture of 45-55% (w/w) of 3-(5-chloro-2H-benzotriazol-2-yl)-5-(1,1-dimethylethyl)-4-hydroxy-phenylpropionic acid octylester and 45-55% (w/w) 3-(5-chloro-2H-benzotriazol-2-yl)-5-(1,1-dimethylethyl)-4-hydroxy-phenylpropionic acid octylester-2-ethylhexylester.

Tinuvin® 1130: a commercially available UV filter (CIBA AG) from the class of benzotriazoles [3-[3-(2H-benzotriazol-2-yl)-5-(1,1-dimethylethyl)-4-hydroxyphenyl]-1-oxopropyl]-w-[3-[3-(2H benzotriazol-2-yl)-5-(1,1-dimethylethyl)-4-hydroxyphenyl]-1-oxopropoxy]poly(oxy-1,2-ethanediyl) of the formula

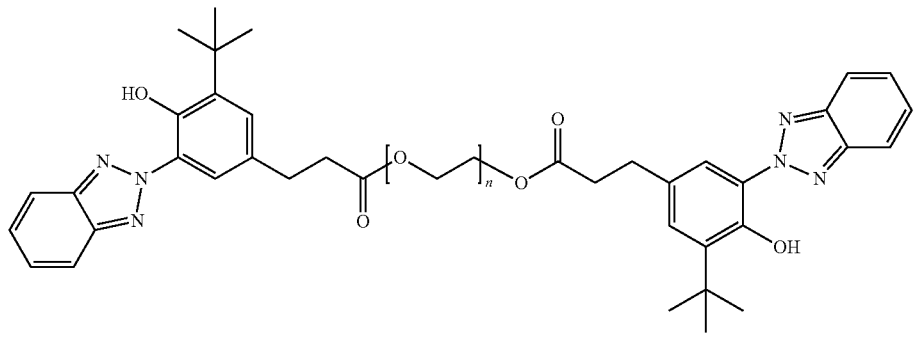

n = 6-7

Uvinul® P25: a commercially available UV filter (BASF SE) p-aminobenzoic acid ethoxylate (45) (mol. wt. Ca. 1,265 g/mol)

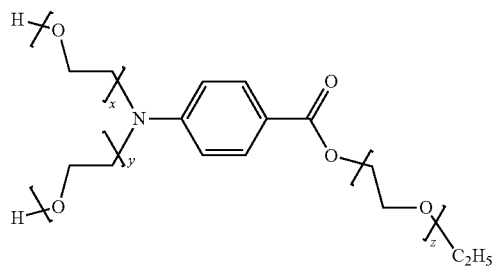

Uvinul® P25

Tinuvin® 99, Tinuvin® 384-2: commercially available UV filters (CAS-No. 127519-17-9; CIBA AG) of formula

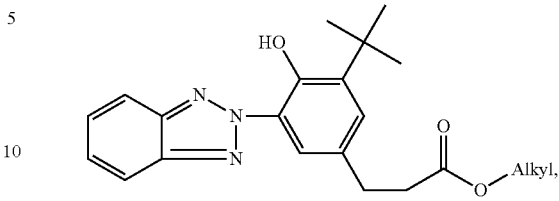

wherein alkyl means a mixture of straight-chain and/or branched C$_7$-C$_9$-alkyl groups.

Tinuvin® R 796: a commercially available UV filter (CIBA AG) from the class of benzotriazoles (CAS-No. 96478-09-0):

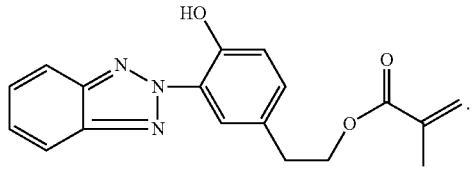

Tinuvin® R 796

Further suitable organic UV filter are to be found in the document "Cosmetic Legislation", Vol. 1, Cosmetic Products, European Commission 1999, 64-66, which is referred to herewith. Suitable organic UV filters are also found in lines 14 to 30 ([0030]) on page 6 of the document EP 1 191 041 A2, which is also referred to herewith and forms part of the disclosure of the present inventions.

Further examples for suitable UV filters are:
belonging to class A) of benzotriazoles or 2-(2'-Hydroxyphenyl)benzotriazoles, such as 2-(2H-benzotriazole-2-yl)-4-methyl-6-(2-methyl-3-((1,1,3,3-tetramethyl-1-(trimethylsilyloxy)disiloxanyl)-propyl)phenol, 2-(2'-hydroxy-5'-methylphenyl)benzotriazole, 2-(3',5'-di-tert.-butyl-2'-hydroxyphenyl)benzotriazole, 2-(5'-tert.-butyl-2'-hydroxyphenyl)benzotriazole, 2-[2'-hydroxy-5-(1,1,3,3-tetramethylbutyl)phenyl]benzotriazole, 2-(3',5'-di-tert.-butyl-2'-hydroxyphenyl)-5-chlorobenzotriazole, 2-(3'-tert.-butyl-2'-hydroxy-5'-methylphenyl)-5-chlorobenzotriazole, 2-(3'-sec.-butyl-5'-tert.-butyl-2'-hydroxyphenyl)benzotriazole, 2-(2'-hydroxy-4'-octyloxyphenyl)benzotriazole, 2-(3',5'-di-tert.-amyl-2'- hydroxyphenyl)benzotriazole, 2-[3',5'-bis(α,α-dimethylbenzyl)-2'-hydroxyphenyl]benzotriazole, 2-[3'-tert.-butyl-2'-hydroxy-5'-(2-octyloxycarbonyl-ethyl)phenyl]-5-chlorobenzotriazole, 2-[3'-tert.-butyl-5'-(2-(2-ethylhexyloxy)-carbonylethyl)-2'-hydroxyphenyl]-5-chlorobenzotriazole, 2-[3'-tert.-butyl-2'-hydroxy-5'-(2-methoxycarbonylethyl)-phenyl]-5-chlorobenzotriazole, 2-[3'-tert.-butyl-2'-hydroxy-5'-(2-methoxycarbonylethyl)-phenyl]benzotriazole, 2-[3'-tert.-butyl-2'-hydroxy-5'-(2-octyloxycarbonylethyl) phenyl]-benzotriazole, 2-[3'-tert.-butyl-5'-(2-(2-ethylhexyloxy)carbonylethyl)-2'-hydroxyphenyl]-benzotriazole, 2-(3'-dodecyl-2'-hydroxy-5'-methylphenyl)benzotriazole, 2-[3'-tert.-butyl-2'-hydroxy-5'-(2-isooctyloxycarbonylethyl)phenyl] benzotriazole, 2,2'-methylen-bis[4-(1,1,3,3-tetramethylbutyl)-6-benzotriazol-2-yl-phenol], esterfied product of 2-[3'-tert.-butyl-5'-(2-methoxycarbonylethyl)-2'-hydroxyphenyl]-2H-benzotriazole and polyethylenglycol 300, [R—CH$_2$CH$_2$—COO(CH$_2$)$_3$—]$_2$ with R being 3'-tert.-butyl-4-hydroxy-5'-2H-benzotriazol-2-ylphenyl, 2-[2'-hydroxy-3'-(α,α-dimethylbenzyl)-5'-(1,1,3,3-tetramethyl butyl)phenyl] benzotriazole, 2-[2'-hydroxy-3'-(1,1,3,3-tetramethylbutyl)-5'-(α,α-dimethylbenzyl)phenyl] benzotriazole;

substituted acrylates, such as ethyl- or isooctyl-α-cyano-β,β-diphenylacrylate, 2-ethylhexyl-α-cyano-β,β-diphenylacrylate, methyl-α-methoxycarbonyl-β-phenyl-acrylate, methyl-α-methoxycarbonyl-β-(p-methoxyphenyl)acrylate, methyl- or butyl-α-cyano-6-methyl-6-(p-methoxyphenyl)acrylate, N-(β-methoxycarbonyl-β-cyanovinyl)-2-methylindoline, octyl-p-methoxycinnamate, isopentyl-4-methoxycinnamate, urocnanic acid or salts and/or esters thereof;

esters of 4,4-diphenylbutadien-1,1-dicarbon acids, such as bis(2-ethylhexyl)ester;

derivatives of bezoxazoles;

α-(2-oxoborn-3-ylidene)toluol-4-sulfonic acid or its salts, N,N,N-trimethyl-4-(2-oxoborn-3-ylidenmethyl) anilinium-monosulfate;

dibenzoylmethanes, such as 4-tert.-butyl-4'-methoxy-dibenzoylmethane;

belonging to class J) of triazine derivatives, such as 2,4,6-Tris-{N-[4-(2-ethylhex-1-yl)oxycarbonylphenyl]amino}-1,3,5-triazine, 4,4'-((6-(((tert.-butyl)aminocarbonyl)-phenylamino)-1,3,5-triazin-2,4-diyl)imino)bis(benzoic acid-2'-ethylhexylester); 2,4,6-tris(2-hydroxy-4-octyloxyphenyl)1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis-(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-Hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis-(2,4-dimethylphenyl)-1,3,5-triazine, 2-(2-hydroxy-4-tridecyloxyphenyl)-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-Hydroxy-4(2-hydroxy-3-dodecyloxypropoxy)phenyl]-4,6-bis-(2,4-dimethylphenyl)-1,3,5-triazine, 2-(2-Hydroxy-4-hexyloxyphenyl)-4,6-diphenyl-1,3,5-triazine, 2-(2-hydroxy-4-methoxyphenyl)4,6-diphenyl-1,3,5-triazine, 2,4,6-Tris[2-hydroxy-4-(3-butoxy-2-hydroxypropoxy)phenyl]-1,3,5-triazine, 2-(2-hydroxy-phenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

The term "UV filters" is understood as meaning organic substances which are able to absorb ultraviolet rays and give off the absorbed energy again in the form of longer-wave radiation, e.g. heat. The term "UV filter" relates to one type or a mixture of different types of said compounds.

For the use as UV filters, organic substances from the groups A) to N) and mixtures thereof as described above are preferred.

The UV filters may be oil-soluble or water-soluble or they may be bound to a polymer, water-soluble UV filters such as compounds of classes A) and F) being preferred.

Preferable, UV filter absorb light of wavelengths between 200 and 600 nm.

The UV filters may be UV-A and UV-B filters, preferably UV-B filters.

The UV filters may also be mixtures of UV filters from groups A) to O).

According to another embodiment, benzotriazole UV filters from group A) are preferred.

The UV filters and the compositions according to the invention, respectively, are suitable for reducing sunburn damage.

The UV filters and the compositions according to the invention are particularly important in reduction of sunburn damage on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and the crop material of these plants.

Preferably, UV filters and compositions thereof, respectively are used in cereals, fruits, trees and vegetables. More preferably, UV filters are used for reducing sunburn damage in cereals and fruits, even more preferably in wheat, barley, tomatoes, apples and pineapples, in particular in barley.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).

Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against Phytophthora infestans derived from the mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

In addition, the present invention provides a method of reducing abiotic lightdependent sunburn damage, such as wilting, chloroses, necroses, and spotting of the areal parts, in a crop plant, where the method comprises, identifying a crop plant in need of sunburn prevention or reduction, and contacting the plant with an effective amount of a composition comprising a UV filter, whereby the sunburn damage of the crop plant is reduced.

The UV filters are employed as such or in form of compositions by treating the plants to be protected with an effective amount of the active substances (UV filters).

The invention also relates to agrochemical compositions comprising a solvent or solid carrier and at least one UV filter.

An agrochemical composition comprises a fungicidally effective amount of a UV filter. The term "effective amount" denotes an amount of the composition or of the UV filters, which is sufficient for reducing sunburn damage or preventing the symptom development on cultivated plants and which does not result in a substantial damage to the treated plants. Such an amount can vary in a broad range and is dependent on various factors, such as the environmental conditions, the treated cultivated plant or cultivar and the specific UV filter used.

The UV filters can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, EC, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144, 050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

Preferably, UV filters may be converted into emulsifiable concentrate type of compositions.

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkyl-sulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzyl-alcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the UV filters and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:
1. Composition Types for Dilution with Water
    i) Water-Soluble Concentrates (SL, LS)
    10 parts by weight of a UV filter according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.
    ii) Dispersible Concentrates (DC)
    20 parts by weight of a UV filter according to the invention are dissolved in 70 parts by weight of cyclohexanone with addition of 10 parts by weight of a dispersant, e.g. polyvinylpyrrolidone. Dilution with water gives a dispersion. The active substance content is 20% by weight.
    iii) Emulsifiable Concentrates (EC)
    15 parts by weight of a UV filter according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
    iv) Emulsions (EW, EO, ES)
    25 parts by weight of a UV filter according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.
    v) Suspensions (SC, OD, FS)
    In an agitated ball mill, 20 parts by weight of a UV filter according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.
    vi) Water-Dispersible Granules and Water-Soluble Granules (WG, SG)
    50 parts by weight of a UV filter according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.
    vii) Water-Dispersible Powders and Water-Soluble Powders (WP, SP, SS, WS)
    75 parts by weight of a UV filter according to the invention are ground in a rotor-stator mill with addition of 25 parts by weight of dispersants, wetting agents and silica gel. Dilution with water gives a stable dispersion or solution of the active substance. The active substance content of the composition is 75% by weight.
    viii) Gel (GF)
    In an agitated ball mill, 20 parts by weight of a UV filter according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.
2. Composition Types to be Applied Undiluted
    ix) Dustable Powders (DP, DS)
    5 parts by weight of a UV filter according to the invention are ground finely and mixed intimately with 95 parts by weight of finely divided kaolin. This gives a dustable composition having an active substance content of 5% by weight.
    x) Granules (GR, FG, GG, MG)
    0.5 parts by weight of a UV filter according to the invention is ground finely and associated with 99.5 parts by weight of carriers. Current methods are extrusion, spray-drying or the fluidized bed. This gives granules to be applied undiluted having an active substance content of 0.5% by weight.
    xi) ULV Solutions (UL)
    10 parts by weight of a UV filter according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 10 and 80%, by weight of active substance (UV filter). The active substances are employed in a purity of from 90% to 100%, preferably from 95% to 100% (according to NMR spectrum).

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts of UV filters applied are, depending on the kind of effect desired, from 0.001 to 2 kg per ha, preferably from 0.005 to 2 kg per ha, more preferably from 0.05 to 0.9 kg per ha, in particular from 0.25 to 0.75 kg per ha.

Various types of oils, wetters, adjuvants, herbicides, bactericides, fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention comprising UV filters as defined herein can, also be present together with other active substances, e.g. with herbicides, insecticides, growth regulators, fungicides or else with fertilizers, as pre-mix or, if appropriate, not until immediately prior to use (tank mix).

Mixing the UV filters or the compositions comprising them with other active substances such as fungicides and/or inorganic substances results in many cases in an increase of the reduction of sunburn damage being obtained. Furthermore, in many cases, synergistic effects are obtained.

It is a further object of the present invention to provide, with a view to effective control of sunburn damage, at application rates which are as low as possible, treatments with compositions which, at a reduced total amount of active compounds applied, have improved activity against sunburn damage.

We have accordingly found that this object is achieved by agrochemical compositions comprising a compound UV filter as defined herein and a solvent or solid carrier and a further active compound II selected from groups A') to G'):

A') Strobilurins
  azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxy-imino-N-methyl-acetamide, 3-methoxy-2-(2-(N-(4-methoxy-phenyl)-cyclopropane-carboximidoylsulfanylmethyl)-phenyl)-acrylic acid methyl ester, methyl(2-chloro-5-[1-(3-methylbenzyloxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide;

B') carboxamides
  carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;
  carboxylic morpholides: dimethomorph, flumorph, pyrimorph;
  benzoic acid amides: flumetover, fluopicolide, fluopyram, zoxamide, N-(3-Ethyl-3,5,5-trimethyl-cyclohexyl)-3-formylamino-2-hydroxy-benzamide;
  other carboxamides: carpropamid, dicyclomet, mandiproamid, oxytetracyclin, silthiofarm and N-(6-methoxy-pyridin-3-yl)cyclopropanecarboxylic acid amide;

C') Azoles
  triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;
  imidazoles: cyazofamid, imazalil, pefurazoate, prochloraz, triflumizol;
  benzimidazoles: benomyl, carbendazim, fuberidazole, thiabendazole;
  others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D') Heterocyclic Compounds
  pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloronicotinamide;
  pyrimidines: bupirimate, cyprodinil, diflumetorim, fenarimol, ferimzone, mepanipyrim, nitrapyrin, nuarimol, pyrimethanil;
  piperazines: triforine;
  pyrroles: fenpiclonil, fludioxonil;
  morpholines: aldimorph, dodemorph, dodemorph-acetate, fenpropimorph, tridemorph;
  piperidines: fenpropidin;
  dicarboximides: fluoroimid, iprodione, procymidone, vinclozolin;
  non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;
  others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E') Carbamates
thio- and dithiocarbamates: ferbam, mancozeb, maneb, metam, methasulphocarb, metiram, propineb, thiram, zineb, ziram;
carbamates: benthiavalicarb, diethofencarb, iprovalicarb, propamocarb, propamocarb hydrochlorid, valiphenal and N-(1-(1-(4-cyano-phenyl)ethanesulfonyl)-but-2-yl) carbamic acid-(4-fluorophenyl)ester;

F') Other Active Substances
guanidines: guanidine, dodine, dodine free base, guazatine, guazatine-acetate, iminoctadine, iminoctadine-triacetate, iminoctadine-tris(albesilate);
antibiotics: kasugamycin, kasugamycin hydrochloride-hydrate, streptomycin, polyoxine, validamycin A;
nitrophenyl derivates: binapacryl, dinobuton, dinocap, nitrthal-isopropyl, tecnazen, organometal compounds: fentin salts, such as fentin-acetate, fentin chloride or fentin hydroxide;
sulfur-containing heterocyclyl compounds: dithianon, isoprothiolane;
organophosphorus compounds: edifenphos, fosetyl, fosetyl-aluminum, iprobenfos, phosphorous acid and its salts, pyrazophos, tolclofos-methyl;
organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
inorganic active substances: Bordeaux mixture, copper acetate, copper hydroxide, copper oxychloride, basic copper sulfate, sulfur;
others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester; and G') Inorganic Substances: Kaolin, Such as Surround® (BASF SE), Metal Oxides, Such as $TiO_2$, ZnO and $CeO_2$.

The present invention furthermore relates to agrochemical compositions comprising a mixture of at least one UV filter (component 1) and at least one fungicide, e.g. one or more fungicide from the groups A') to F'), as described above, and if desired one suitable solvent or solid carrier. In another preferred embodiment the agrochemical compositions comprises a mixture of at least one UV filter (component 1) and at least one fungicide (such as one, two, three, four or five) from the groups A') to F'), as described above, and if desired one suitable solvent or solid carrier.

In the compositions comprising a UV filter and a further active compound II, the UV filter/compound II ratio is advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

In binary mixtures, i.e. compositions according to the invention comprising one UV filter (component 1) and one further active substance (component 2), e.g. one active substance from groups A) to I), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially premixed components, e.g. components comprising UV filters and/or active substances from the groups A') to G'), may be mixed by the user in a spray tank and further auxiliaries and additives may be added, if appropriate (tank mix)

In a further embodiment, either individual components of the composition according to the invention or partially premixed components, e.g. components comprising UV filters and/or active substances from the groups A') to G'), can be applied jointly (e.g. after tankmix) or consecutively.

Preference is also given to mixtures comprising a UV filter (component 1) and at least one active substance selected from the strobilurines of group A') (component 2) and particularly selected from azoxystrobin, dimoxystrobin, fluoxastrobin, kresoxim-methyl, orysastrobin, picoxystrobin, pyraclostrobin and trifloxystrobin.

Preference is also given to mixtures comprising a UV filter (component 1) and at least one active substance selected from the carboxamides of group B') (component 2) and particularly selected from bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid and N-(3',4',5'-trifluorobiphenyl-2-yl)-3-difluoromethyl-1-methyl-1H-pyrazole-4-carboxamide.

Preference is given to mixtures comprising a UV filter (component 1) and at least one active substance selected from the azoles of group C') (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Preference is also given to mixtures comprising a UV filter (component 1) and at least one active substance selected from the heterocyclic compounds of group D') (component 2) and particularly selected from fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen and 5-ethyl-6-octyl-[1,2,4]triazolo[1,5-a]pyrimidine-7-ylamine.

Preference is also given to mixtures comprising a UV filter (component 1) and at least one active substance selected from the carbamates of group E') (component 2) and particularly selected from mancozeb, metiram, propineb, thiram, iprovalicarb, benthiavalicarb and propamocarb.

Preference is also given to mixtures comprising a UV filter (component 1) and at least one active substance selected from the fungicides given in group F') (component 2) and particularly selected from dithianon, fentin salts, such as fentin acetate, fosetyl, fosetyl-aluminium, $H_3PO_3$ and salts thereof, chlorthalonil, dichlofluanid, thiophanatmethyl, copper acetate, copper hydroxide, copper oxychloride, copper sulfate, sulfur, cymoxanil, metrafenone and spiroxamine.

Preference is also given to mixtures comprising a UV filter (component 1) and at least one active substance selected from the anorganic compounds of group G'), preferably kaolin, more preferably Surround®.

Accordingly, the present invention furthermore relates to compositions comprising one UV filter (component 1) and one further active substance (component 2), which further active substance is selected from the column "Component 2" of the lines B-1 to B-246 of Table B.

A further embodiment relates to the compositions B-1 to B-246 listed in Table B, where a row of Table B corresponds in each case to a fungicidal composition comprising one of the in the present specification individualized UV filters (component 1) and the respective further active substance from groups A') to F') (component 2) stated in the row in question. Preferably, the compositions described comprise the active substances in synergistically effective amounts.

TABLE B

Composition comprising one UV filter and one further active substance from groups A') to F')

| Mixture | Component 1 | Component 2 |
|---|---|---|
| B-1 | one UV filter as defined herein | Azoxystrobin |
| B-2 | one UV filter as defined herein | Dimoxystrobin |
| B-3 | one UV filter as defined herein | Enestroburin |
| B-4 | one UV filter as defined herein | Fluoxastrobin |
| B-5 | one UV filter as defined herein | Kresoxim-methyl |
| B-6 | one UV filter as defined herein | Metominostrobin |
| B-7 | one UV filter as defined herein | Orysastrobin |
| B-8 | one UV filter as defined herein | Picoxystrobin |
| B-9 | one UV filter as defined herein | Pyraclostrobin |
| B-10 | one UV filter as defined herein | Pyribencarb |
| B-11 | one UV filter as defined herein | Trifloxystrobin |
| B-12 | one UV filter as defined herein | 2-(2-(6-(3-Chloro-2-methyl-phenoxy)-5-fluoro-pyrimidin-4-yloxy)-phenyl)-2-methoxyimino-N-methyl-acetamide |
| B-13 | one UV filter as defined herein | 2-(ortho-((2,5-Dimethylphenyl-oxymethylen)phenyl)-3-methoxy-acrylsäuremethylester |
| B-14 | one UV filter as defined herein | 3-Methoxy-2-(2-(N-(4-methoxy-phenyl)-cyclopropanecarboximidoylsulfanyl-methyl)-phenyl)-acrylic acid methyl ester |
| B-15 | one UV filter as defined herein | 2-(2-(3-(2,6-dichlorophenyl)-1-methyl-allylideneaminooxymethyl)-phenyl)-2-methoxyimino-N-methyl-acetamide |
| B-16 | one UV filter as defined herein | Benalaxyl |
| B-17 | one UV filter as defined herein | Benalaxyl-M |
| B-18 | one UV filter as defined herein | Benodanil |
| B-19 | one UV filter as defined herein | Bixafen |
| B-20 | one UV filter as defined herein | Boscalid |
| B-21 | one UV filter as defined herein | Carboxin |
| B-22 | one UV filter as defined herein | Fenfuram |
| B-23 | one UV filter as defined herein | Fenhexamid |
| B-24 | one UV filter as defined herein | Flutolanil |
| B-25 | one UV filter as defined herein | Furametpyr |
| B-26 | one UV filter as defined herein | Isopyrazam |
| B-27 | one UV filter as defined herein | Isotianil |
| B-28 | one UV filter as defined herein | Kiralaxyl |
| B-29 | one UV filter as defined herein | Mepronil |
| B-30 | one UV filter as defined herein | Metalaxyl |
| B-31 | one UV filter as defined herein | Metalaxyl-M |
| B-32 | one UV filter as defined herein | Ofurace |
| B-33 | one UV filter as defined herein | Oxadixyl |

TABLE B-continued

Composition comprising one UV filter and one further active substance from groups A') to F')

| Mixture | Component 1 | Component 2 |
|---|---|---|
| B-34 | one UV filter as defined herein | Oxycarboxin |
| B-35 | one UV filter as defined herein | Penthiopyrad |
| B-36 | one UV filter as defined herein | Sedaxane |
| B-37 | one UV filter as defined herein | Tecloftalam |
| B-38 | one UV filter as defined herein | Thifluzamide |
| B-39 | one UV filter as defined herein | Tiadinil |
| B-40 | one UV filter as defined herein | 2-Amino-4-methyl-thiazole-5-carboxylic acid anilide |
| B-41 | one UV filter as defined herein | 2-Chloro-N-(1,1,3-trimethyl-indan-4-yl)-nicotinamide |
| B-42 | one UV filter as defined herein | N-(3',4',5'-trifluorobiphenyl-2-yl)-3-difluoromethyl-1-methyl-1H-pyrazole-4-carboxamide |
| B-43 | one UV filter as defined herein | N-(4'-trifluoromethylthiobiphenyl-2-yl)-3-difluoromethyl-1-methyl-1H-pyrazole-4-carboxamide |
| B-44 | one UV filter as defined herein | N-(2-(1,3-dimethyl-butyl)-phenyl)-1,3-dimethyl-5-fluoro-1H-pyrazole-4-carboxamide |
| B-45 | one UV filter as defined herein | N-(2-(1,3,3-trimethyl-butyl)-phenyl)-1,3-dimethyl-5-fluoro-1H-pyrazole-4-carboxamide |
| B-46 | one UV filter as defined herein | Dimethomorph |
| B-47 | one UV filter as defined herein | Flumorph |
| B-48 | one UV filter as defined herein | Pyrimorph |
| B-49 | one UV filter as defined herein | Flumetover |
| B-50 | one UV filter as defined herein | Fluopicolide |
| B-51 | one UV filter as defined herein | Fluopyram |
| B-52 | one UV filter as defined herein | Zoxamide |
| B-53 | one UV filter as defined herein | N-(3-Ethyl-3,5,5-trimethyl-cyclohexyl)-3-formylamino-2-hydroxy-benzamide |
| B-54 | one UV filter as defined herein | Carpropamid |
| B-55 | one UV filter as defined herein | Diclocymet |
| B-56 | one UV filter as defined herein | Mandipropamid |
| B-57 | one UV filter as defined herein | Oxytetracyclin |
| B-58 | one UV filter as defined herein | Silthiofam |
| B-59 | one UV filter as defined herein | N-(6-methoxy-pyridin-3-yl) cyclopropanecarboxylic acid amide |
| B-60 | one UV filter as defined herein | Azaconazole |
| B-61 | one UV filter as defined herein | Bitertanol |
| B-62 | one UV filter as defined herein | Bromuconazole |
| B-63 | one UV filter as defined herein | Cyproconazole |
| B-64 | one UV filter as defined herein | Difenoconazole |
| B-65 | one UV filter as defined herein | Diniconazole |
| B-66 | one UV filter as defined herein | Diniconazole-M |
| B-67 | one UV filter as defined herein | Epoxiconazole |
| B-68 | one UV filter as defined herein | Fenbuconazole |
| B-69 | one UV filter as defined herein | Fluquinconazole |
| B-70 | one UV filter as defined herein | Flusilazole |
| B-71 | one UV filter as defined herein | Flutriafol |
| B-72 | one UV filter as defined herein | Hexaconazol |
| B-73 | one UV filter as defined herein | Imibenconazole |
| B-74 | one UV filter as defined herein | Ipconazole |
| B-75 | one UV filter as defined herein | Metconazole |
| B-76 | one UV filter as defined herein | Myclobutanil |
| B-77 | one UV filter as defined herein | Oxpoconazol |
| B-78 | one UV filter as defined herein | Paclobutrazol |
| B-79 | one UV filter as defined herein | Penconazole |
| B-80 | one UV filter as defined herein | Propiconazole |
| B-81 | one UV filter as defined herein | Prothioconazole |
| B-82 | one UV filter as defined herein | Simeconazole |
| B-83 | one UV filter as defined herein | Tebuconazole |
| B-84 | one UV filter as defined herein | Tetraconazole |
| B-85 | one UV filter as defined herein | Triadimefon |
| B-86 | one UV filter as defined herein | Triadimenol |
| B-87 | one UV filter as defined herein | Triticonazole |
| B-88 | one UV filter as defined herein | Uniconazole |
| B-89 | one UV filter as defined herein | 1-(4-Chloro-phenyl)-2-([1,2,4]triazol-1-yl)-cycloheptanol |
| B-90 | one UV filter as defined herein | Cyazofamid |
| B-91 | one UV filter as defined herein | Imazalil |
| B-92 | one UV filter as defined herein | Imazalil-sulfate |
| B-93 | one UV filter as defined herein | Pefurazoate |
| B-94 | one UV filter as defined herein | Prochloraz |
| B-95 | one UV filter as defined herein | Triflumizole |

TABLE B-continued

Composition comprising one UV filter and one further active substance from groups A') to F')

| Mixture | Component 1 | Component 2 |
|---|---|---|
| B-96 | one UV filter as defined herein | Benomyl |
| B-97 | one UV filter as defined herein | Carbendazim |
| B-98 | one UV filter as defined herein | Fuberidazole |
| B-99 | one UV filter as defined herein | Thiabendazole |
| B-100 | one UV filter as defined herein | Ethaboxam |
| B-101 | one UV filter as defined herein | Etridiazole |
| B-102 | one UV filter as defined herein | Hymexazole |
| B-103 | one UV filter as defined herein | 2-(4-Chloro-phenyl)-N-[4-(3,4-dimethoxy-phenyl)-isoxazol-5-yl]-2-prop-2-ynyloxy-acetamide |
| B-104 | one UV filter as defined herein | Fluazinam |
| B-105 | one UV filter as defined herein | Pyrifenox |
| B-106 | one UV filter as defined herein | 3-[5-(4-Chloro-phenyl)-2,3-dimethyl-isoxazolidin-3-yl]-pyridine |
| B-107 | one UV filter as defined herein | 3-[5-(4-Methyl-phenyl)-2,3-dimethyl-isoxazolidin-3-yl]-pyridine |
| B-108 | one UV filter as defined herein | 2,3,5,6-Tetrachloro-4-methanesulfonyl-pyridine |
| B-109 | one UV filter as defined herein | 3,4,5-Trichloro-pyridine-2,6-dicarbonitrile |
| B-110 | one UV filter as defined herein | N-(1-(5-Bromo-3-chloro-pyridin-2-yl)-ethyl)-2,4-dichloro-nicotinamide |
| B-111 | one UV filter as defined herein | N-((5-Bromo-3-chloro-pyridin-2-yl)-methyl)-2,4-dichloro-nicotinamide |
| B-112 | one UV filter as defined herein | Bupirimate |
| B-113 | one UV filter as defined herein | Cyprodinil |
| B-114 | one UV filter as defined herein | Diflumetorim |
| B-115 | one UV filter as defined herein | Fenarimol |
| B-116 | one UV filter as defined herein | Ferimzone |
| B-117 | one UV filter as defined herein | Mepanipyrim |
| B-118 | one UV filter as defined herein | Nitrapyrin |
| B-119 | one UV filter as defined herein | Nuarimol |
| B-120 | one UV filter as defined herein | Pyrimethanil |
| B-121 | one UV filter as defined herein | Triforine |
| B-122 | one UV filter as defined herein | Fenpiclonil |
| B-123 | one UV filter as defined herein | Fludioxonil |
| B-124 | one UV filter as defined herein | Aldimorph |
| B-125 | one UV filter as defined herein | Dodemorph |
| B-126 | one UV filter as defined herein | Dodemorph-acetate |
| B-127 | one UV filter as defined herein | Fenpropimorph |
| B-128 | one UV filter as defined herein | Tridemorph |
| B-129 | one UV filter as defined herein | Fenpropidin |
| B-130 | one UV filter as defined herein | Fluoroimid |
| B-131 | one UV filter as defined herein | Iprodione |
| B-132 | one UV filter as defined herein | Procymidone |
| B-133 | one UV filter as defined herein | Vinclozolin |
| B-134 | one UV filter as defined herein | Famoxadone |
| B-135 | one UV filter as defined herein | Fenamidone |
| B-136 | one UV filter as defined herein | Flutianil |
| B-137 | one UV filter as defined herein | Octhilinone |
| B-138 | one UV filter as defined herein | Probenazole |
| B-139 | one UV filter as defined herein | 5-Amino-2-iso-propyl-4-ortho-tolyl-2,3-dihydro-pyrazole-1-carbothioic acid S-allyl ester |
| B-140 | one UV filter as defined herein | Acibenzolar-S-methyl |
| B-141 | one UV filter as defined herein | Amisulbrom |
| B-142 | one UV filter as defined herein | Anilazin |
| B-143 | one UV filter as defined herein | Blasticidin-S |
| B-144 | one UV filter as defined herein | Captafol |
| B-145 | one UV filter as defined herein | Captan |
| B-146 | one UV filter as defined herein | Chinomethionat |
| B-147 | one UV filter as defined herein | Dazomet |
| B-148 | one UV filter as defined herein | Debacarb |
| B-149 | one UV filter as defined herein | Diclomezine |
| B-150 | one UV filter as defined herein | Difenzoquat, |
| B-151 | one UV filter as defined herein | Difenzoquat-methylsulfate |
| B-152 | one UV filter as defined herein | Fenoxanil |
| B-153 | one UV filter as defined herein | Folpet |
| B-154 | one UV filter as defined herein | Oxolinsäure |
| B-155 | one UV filter as defined herein | Piperalin |
| B-156 | one UV filter as defined herein | Proquinazid |
| B-157 | one UV filter as defined herein | Pyroquilon |
| B-158 | one UV filter as defined herein | Quinoxyfen |
| B-159 | one UV filter as defined herein | Triazoxid |
| B-160 | one UV filter as defined herein | Tricyclazole |

TABLE B-continued

Composition comprising one UV filter and one further active substance from groups A') to F')

| Mixture | Component 1 | Component 2 |
|---|---|---|
| B-161 | one UV filter as defined herein | 2-Butoxy-6-iodo-3-propyl-chromen-4-one |
| B-162 | one UV filter as defined herein | 5-Chloro-1-(4,6-dimethoxy-pyrimidin-2-yl)-2-methyl-1H-benzoimidazole |
| B-163 | one UV filter as defined herein | 5-Chloro-7-(4-methyl-piperidin-1-yl)-6-(2,4,6-trifluoro-phenyl)-[1,2,4]triazolo[1,5-a]pyrimidine |
| B-164 | one UV filter as defined herein | 5-ethyl-6-octyl-[1,2,4]triazolo[1,5-a]pyrimidine-7-ylamine |
| B-165 | one UV filter as defined herein | Ferbam |
| B-166 | one UV filter as defined herein | Mancozeb |
| B-167 | one UV filter as defined herein | Maneb |
| B-168 | one UV filter as defined herein | Metam |
| B-169 | one UV filter as defined herein | Methasulphocarb |
| B-170 | one UV filter as defined herein | Metiram |
| B-171 | one UV filter as defined herein | Propineb |
| B-172 | one UV filter as defined herein | Thiram |
| B-173 | one UV filter as defined herein | Zineb |
| B-174 | one UV filter as defined herein | Ziram |
| B-175 | one UV filter as defined herein | Diethofencarb |
| B-176 | one UV filter as defined herein | Benthiavalicarb |
| B-177 | one UV filter as defined herein | Iprovalicarb |
| B-178 | one UV filter as defined herein | Propamocarb |
| B-179 | one UV filter as defined herein | Propamocarb hydrochlorid |
| B-180 | one UV filter as defined herein | Valiphenal |
| B-181 | one UV filter as defined herein | N-(1-(1-(4-cyanophenyl)ethanesulfonyl)-but-2-yl) carbamic acid-(4-fluoro-phenyl) ester |
| B-182 | one UV filter as defined herein | Dodine |
| B-183 | one UV filter as defined herein | Dodine free base |
| B-184 | one UV filter as defined herein | Guazatine |
| B-185 | one UV filter as defined herein | Guazatine-acetate |
| B-186 | one UV filter as defined herein | Iminoctadine |
| B-187 | one UV filter as defined herein | Iminoctadine-triacetate |
| B-188 | one UV filter as defined herein | Iminoctadine-tris(albesilate) |
| B-189 | one UV filter as defined herein | Kasugamycin |
| B-190 | one UV filter as defined herein | Kasugamycin-hydrochloride-hydrate |
| B-191 | one UV filter as defined herein | Polyoxine |
| B-192 | one UV filter as defined herein | Streptomycin |
| B-193 | one UV filter as defined herein | Validamycin A |
| B-194 | one UV filter as defined herein | Binapacryl |
| B-195 | one UV filter as defined herein | Dicloran |
| B-196 | one UV filter as defined herein | Dinobuton |
| B-197 | one UV filter as defined herein | Dinocap |
| B-198 | one UV filter as defined herein | Nitrothal-isopropyl |
| B-199 | one UV filter as defined herein | Tecnazen |
| B-200 | one UV filter as defined herein | Fentin salts |
| B-201 | one UV filter as defined herein | Dithianon |
| B-202 | one UV filter as defined herein | Isoprothiolane |
| B-203 | one UV filter as defined herein | Edifenphos |
| B-204 | one UV filter as defined herein | Fosetyl, Fosetyl-aluminium |
| B-205 | one UV filter as defined herein | Iprobenfos |
| B-206 | one UV filter as defined herein | Phosphorous acid ($H_3PO_3$) and derivatives |
| B-207 | one UV filter as defined herein | Pyrazophos |
| B-208 | one UV filter as defined herein | Tolclofos-methyl |
| B-209 | one UV filter as defined herein | Chlorothalonil |
| B-210 | one UV filter as defined herein | Dichlofluanid |
| B-211 | one UV filter as defined herein | Dichlorophen |
| B-212 | one UV filter as defined herein | Flusulfamide |
| B-213 | one UV filter as defined herein | Hexachlorbenzene |
| B-214 | one UV filter as defined herein | Pencycuron |
| B-215 | one UV filter as defined herein | Pentachlorophenol and salts |
| B-216 | one UV filter as defined herein | Phthalide |
| B-217 | one UV filter as defined herein | Quintozene |
| B-218 | one UV filter as defined herein | Thiophanate Methyl |
| B-219 | one UV filter as defined herein | Tolylfluanid |
| B-220 | one UV filter as defined herein | N-(4-chloro-2-nitro-phenyl)-N-ethyl-4-methyl-benzenesulfonamide |
| B-221 | one UV filter as defined herein | Bordeaux mixture |
| B-222 | one UV filter as defined herein | Copper acetate |
| B-223 | one UV filter as defined herein | Copper hydroxide |
| B-224 | one UV filter as defined herein | Copper oxychloride |
| B-225 | one UV filter as defined herein | basic Copper sulfate |
| B-226 | one UV filter as defined herein | Sulfur |

TABLE B-continued

Composition comprising one UV filter and one further active substance from groups A') to F')

| Mixture | Component 1 | Component 2 |
|---|---|---|
| B-227 | one UV filter as defined herein | Biphenyl |
| B-228 | one UV filter as defined herein | Bronopol |
| B-229 | one UV filter as defined herein | Cyflufenamid |
| B-230 | one UV filter as defined herein | Cymoxanil |
| B-231 | one UV filter as defined herein | Diphenylamin |
| B-232 | one UV filter as defined herein | Metrafenone |
| B-233 | one UV filter as defined herein | Mildiomycin |
| B-234 | one UV filter as defined herein | Oxin-copper |
| B-235 | one UV filter as defined herein | Prohexadione calcium |
| B-236 | one UV filter as defined herein | Spiroxamine |
| B-237 | one UV filter as defined herein | Tolylfluanid |
| B-238 | one UV filter as defined herein | N-(Cyclopropylmethoxyimino-(6-difluoromethoxy-2,3-difluoro-phenyl)-methyl)-2-phenyl acetamide |
| B-239 | one UV filter as defined herein | N'-(4-(4-chloro-3-trifluoromethyl-phenoxy)-2,5-dimethyl-phenyl)-N-ethyl-N-methyl formamidine |
| B-240 | one UV filter as defined herein | N'-(4-(4-fluoro-3-trifluoromethyl-phenoxy)-2,5-dimethyl-phenyl)-N-ethyl-N-methyl formamidine |
| B-241 | one UV filter as defined herein | N'-(2-methyl-5-trifluoromethyl-4-(3-tri-methylsilanyl-propoxy)-phenyl)-N-ethyl-N-methyl formamidine |
| B-242 | one UV filter as defined herein | N'-(5-difluoromethyl-2-methyl-4-(3-tri-methylsilanyl-propoxy)-phenyl)-N-ethyl-N-methyl formamidine |
| B-243 | one UV filter as defined herein | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-244 | one UV filter as defined herein | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-245 | one UV filter as defined herein | Acetic acid 6-tert.-butyl-8-fluoro-2,3-dimethyl-quinolin-4-yl ester |
| B-246 | one UV filter as defined herein | Methoxy-acetic acid 6-tert-butyl-8-fluoro-2,3-dimethyl-quinolin-4-yl ester |

The fungicides referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

The mixtures of active substances can be prepared as compositions comprising besides the active ingredients at least one inert ingredient by usual means, e.g. by the means given for the compositions of UV filters.

Concerning usual ingredients of such compositions reference is made to the explanations given for the compositions containing UV filters.

The mixtures of active substances according to the present invention are suitable for reducing sunburn damage, as are the UV filters.

The invention is further illustrated but not limited by the following examples.

EXAMPLES

Uvinul® 3035: Ethyl-2-cyano-3,3-diphenyl acrylate, compound of the structure (4), commercially available as Uvinul® 3035 from BASF SE.

Pluriol® A350E: Polyethylene glycol monomethylether, OH-number 160 mg KOH/g, molar weight of about 350 g/mol, commercially available as Pluriol® A350E from BASF SE.

Tinuvin® 384-2: A commercially available UV filter (from CIBA AG) of the class of hydroxyphenyl benzotriazoles (95% benzenepropanoic acid, 3-(2H-benzotriazol-2-yl)-5-(1,1-dimethylethyl)-4-hydroxy-, $C_{7-9}$-alkyl ester and 5% 1-methoxy-2-propylacetat).

Example 1

Synthesis of UV Filter A (2-Cyano-3,3-diphenyl-acrylsäure-[Pluriol A350E]-ester) (3)

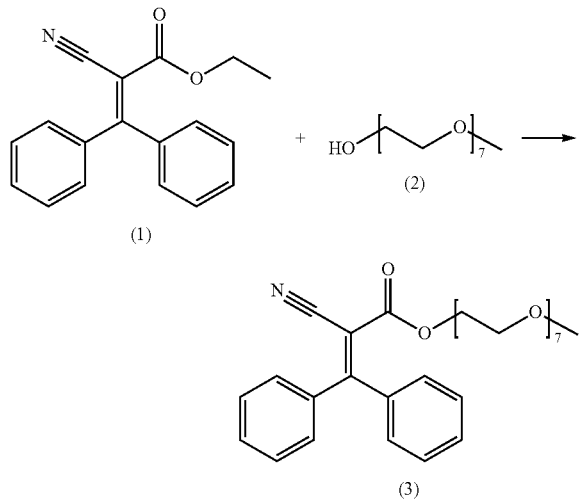

63.4 g (189 mMol) Pluriol A350E (2) were stirred for 30 min at 150° C. under nitrogen and 50.0 g (180 mMol) Uvinul 3035 (1) and 0.58 g (2 mMol) titanium(IV) isopropoxid were added. The mixture was stirred at 155° C. for 24 hours and the resulting ethanol distilled off. 200 ml methylene chloride and 350 mg (3 mMol) phosphoric acid 85% were added and the solution was left at 20° C. for 24 h. The product was purified by flash chromatography on silica. 94 g of an orange viscous liquid (3) was obtained (yield 95%).

Example 2

Synthesis of UV Filter B (3-(3-Benzotriazol-2-yl-5-tert-butyl-4-hydroxyphenyl)-propiosäure-[Pluriol A350E]-ester (5))

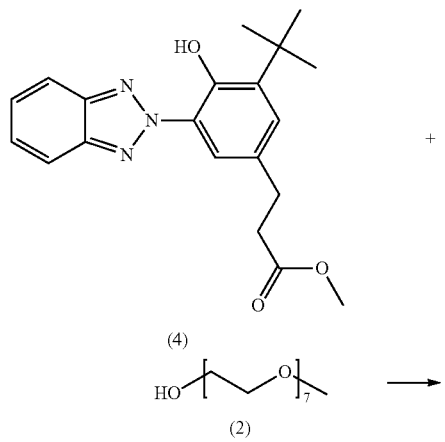

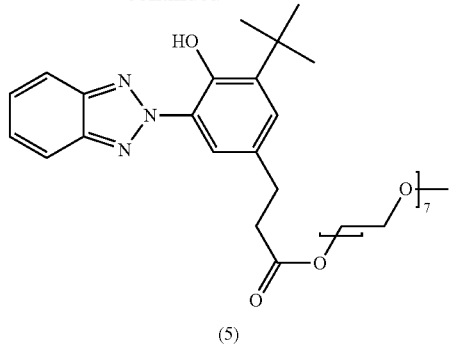

Compound (4) was synthesized according to literature starting from commercially available Tinuvin® 384-2 by hydrolysis and subsequent esterification with methanol.

59.7 g (187 mMol) Pluriol® A350E (2) was stirred for 30 Minutes at 150° C. and 60.0 g (170 mMol) compound (4) and 0.54 g (2 mMol) titanium(IV) isopropoxid added. The mixture was stirred at 155° C. for 18 hours. The resulting methanol was distilled off. 100 mL toluene and 350 mg (3 mMol) phosphoric acid 85% were added and the solution was left standing at 20° C. for 24 h. The product was purified by flash chromatography on silica. 106 g of an orange viscous liquid (5) was obtained (yield=99%).

Example 3

Preventive Action on Winter Barley Against Sunburn Injury

As active substance a mixture of active substances was used called "Actives A & B", which was prepared by mixing Active A and Active B. Active A was a fungicidal suspension concentrate comprising 6 wt % epoxiconazol, 20.8 wt % boscalid, 11.2-12.6 wt % fatty alcohol alkoxylate, C8-alkyl glucoside, and phenolsulfonic acid-formaldehyde-polycondensate sodium salt (commercially available pesticide formulation from BASF SE as Champion®). Active B a fungicidal suspoemulsion comprising 20.6 wt % fenpropimorph, 11 wt % pyraclostrobin, 4.1 wt % epoxiconazol, 20.5 wt % solvent naphtha, 11 wt % fatty alcohol ethoxylate and 4.8 wt % phenolsulfonic acid-formaldehyde-polycondensate sodium salt (commercially available pesticide formulation from BASF SE as Diamant®). UV Filter A and UV filter B were prepared as described in examples 1 and 2.

The biological trial was conducted under field conditions in Germany. Barley was planted and grown under standard conditions with adequate supply of water and nutrients. At BBCH 53 an application of the compounds (see Table 1) was made. The dosages used and the obtained results are shown in Table 1. No other compounds were applied for pathogen control. The level of sunburn injury was evaluated 22 days after application (% estimation of destroyed leaf area).

The sunburn injury assessments were converted into efficacies. An efficacy of 0 means that the sunburn injury level of the treated plants corresponds to that of the untreated control plants; an efficacy of 100 means that the treated plants had no sunburn symptoms. The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

TABLE 1

| Compound | Product rate (L/ha) | Dose rate (g ai/ha) | Ratio[a] | Efficacy | Expected efficacy Colby (%) |
|---|---|---|---|---|---|
| 1 Untreated control | — | — | — | 100% sunburn injury | — |
| 2 UV Filter A | 2 | 500 | — | 4 | — |
| 3 UV Filter B | 2 | 500 | — | 3 | — |
| 4 Actives A & B | 0.8 & 0.8 | 240 & 297 | — | 35 | — |
| 5 UV Filter A + Actives A & B | 2 + 0.8 & 0.8 | 500 + 240 & 297 | 2.5:1:1 | 56 | 37 |
| 6 UV Filter B + Actives A & B | 2 + 0.8 & 0.8 | 500 + 240 & 297 | 2.5:1:1 | 73 | 37 |

[a] Ratio of UV Filter: Active A:Active B

The experiments (line 2 to 6) showed that UV filters reduced sunburn injury in plants compared to untreated plants (line 1). It was also demonstrated a synergistic effect of a mixture comprising an active substance and a UV filter.

Example 4

Preventive Action on Winter Barley Against Sunburn Injury

The biological trial was conducted under field conditions in Germany. The barley cultivar *Campanile* was planted and grown under standard conditions with adequate supply of water and nutrients. At BBCH 37-39, 0.9 l/ha of Actives A & B were applied. At BBCH 49 2.0 l/ha of UV-Filter A or B were applied. The level of sunburn injury was evaluated 22 days after the last application (% estimation of physiological leaf spots, PLS).

The sunburn injury assessments were converted into efficacies. An efficacy of 0 means that the sunburn injury level of the treated plants corresponds to that of the untreated control plants; an efficacy of 100 means that the treated plants had no sunburn symptoms.

TABLE 2

| | Compound | Rating of PLS (%) | Efficacy (%) |
|---|---|---|---|
| 1 | Untreated control | 62 | 0 |
| 2 | Actives A & B | 14 | 78 |
| 3 | UV Filter A + Actives A & B | 10 | 84 |
| 4 | UV Filter B + Actives A & B | 7 | 89 |

The experiments (line 3 and 4) showed that UV filters in combination with active substances are useful for combating harmful fungi in plants compared to untreated plants (line 1) and compared to plants treated with active substances only (line 2).

Example 5

Preventive Action on Winter Barley Against Sunburn Injury

The biological trial was conducted under field conditions in Germany. The barley cultivar *Finita* was planted and grown under standard conditions with adequate supply of water and nutrients. At BBCH 53 0.8 l/ha of Actives A & B and 2.0 l/ha UV Filter A or B were applied. For comparison, the Surround® (commercially available from Engelhard Corp., wettable powder comprising 95 wt % kaolin) was applied at a rate of 10 kg/ha. The level of sunburn injury was evaluated 15 and 22 days after application (% estimation of destroyed leaf area).

TABLE 3

Rating of sun burn injury at two timings

| | Compound | % sunburn injury 15 days after application | % sunburn injury 22 days after application |
|---|---|---|---|
| 1 | Untreated control | 63 | 100 |
| 2 | Surround ® | 44 | 100 |
| 3 | Actives A & B | 16 | 65 |
| 4 | UV Filter A | 38 | 96 |
| 5 | UV Filter B | 36 | 97 |
| 6 | UV Filter A + Actives A & B | 9 | 44 |
| 7 | UV Filter B + Actives A & B | 8 | 28 |

The experiments (line 4 to 7) showed that UV filters, optionally in combination with active substances, are useful to protect plants from sunburn injury compared to untreated plants (line 1). A commercial product Surround®, which is recommended to reduce sunburn damage (based on a natural mineral kaolin) was used for comparison.

The invention claimed is:

1. A method of reducing sunburn damage in a cereal plant where the method comprises identifying a cereal plant in need of reducing sunburn damage, and contacting the plant with an effective amount of a composition comprising at least one UV filter, whereby the sunburn damage of the crop plant is controlled, and wherein the at least UV filter is selected from the group consisting of:

A) benzotriazoles, selected from, [3-[3-(2H-benzotriazol-2-yl)-5-(1,1-dimethylethyl)-4-hydroxyphenyl]-1-oxo-propyl]-w-[3-[3-(2H-benzotriazol-2-yl)-5-(1,1-dimethylethyl)-4-hydroxyphenyl]-1-oxopropoxy]poly(oxy-1,2-ethanediyl), 6-tert.-butyl-2-(5-chloro-2H-benzotriazol-2-yl)-4-methylphenol, 2,4-di-tert-butyl-6-(5-chloro-2H-benzotriazol-2-yl)-phenol, 2-(2H-benzotriazol-2-yl)-4,6-di-tert.-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phen-ylethyl)phenol, and compounds of formula I

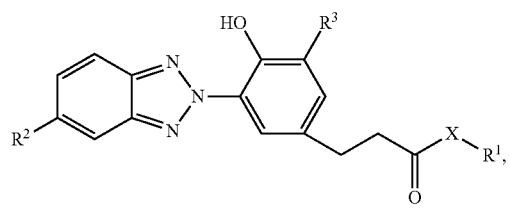

wherein
X is NH or O;
R[1] is [$C_2$-$C_4$-alkoxy]$_n$-($C_1$-$C_{18}$-alkyl) or —[$CH_2CH_2NH$]$_n$—H;
R[2] is H or Cl;
R[3] is H or $C_1$-$C_8$-alkyl; and
n is an integer between 3 and 50;

B) Cyanoacrylate derivatives selected from ethyl 2-cyano-3-phenylcinnamate, 2-cyano-3,3-diphenylacrylic acid-2'-ethylhexyl ester, and compounds of formula

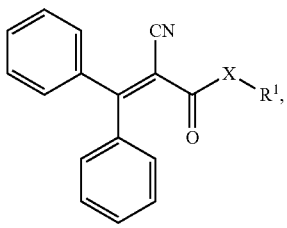

wherein
X is NH or O;
R¹ is [C₂-C₄-alkoxy]ₙ-(C₁-C₁₈-alkyl) or —[CH₂CH₂NH]ₙ—H;
n is an integer between 3 and 50;
C) para-aminobenzoic acid (PABA) derivatives selected from ethyl-PABA, ethoxylated PABA, ethyl-dihydroxypropyl-PABA, Glycerol-PABA, 2-ethylhexyl 4-(dimethylamino)benzoate, 2-octyl 4-(dimethylamino)benzoate, amyl 4-(dimethylamino)benzoate, and 4-bis (polyethoxy)-4-amino benzoic acid polyethoxyethyl ester;
D) esters of salicylic acid selected from 2-ethylhexyl salicylate, 4-isopropylbenzyl salicylate, homomenthyl salicylate, TEA salicylate, and dipropyleneglycol salicylate;
E) esters of cinnamic acid selected from, octyl-p-methoxycinnamate, propyl 4-methoxycinnamate, isoamyl-4-methoxycinnamate, conoxate, diisopropyl methylcinnamate, etocrylene, and compounds of formula

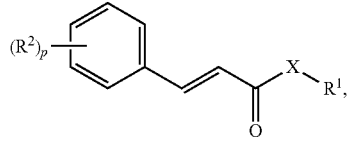

wherein
X is NH or O;
R¹ is H or [C₂-C₄-alkoxy]ₙ-(C₁-C₁₈-alkyl) or —[CH₂CH₂NH]ₙ—H;
R² is OH or C₁-C₈-alkoxy;
p is an integer between 0 and 5; and
n is an integer between 3 and 50;
F) derivatives of benzophenone selected from, 2 hydroxy-4-methoxy-4'-methylbenzophenone, 2-(4-diethylamino-2-hydroxybenzoyl)-benzoic acid hexylester, 4-n-octyloxy-2-hydroxy-benzophenone, 2-hydroxybenophenone derivatives selected from: 4-hydroxy-, 4-methoxy-, 4-octyloxy-, 4-decyloxy-, 4-dodecyloxy-, 4-benzyloxy-, 4,2',4'-trihydroxy-; 2'-hydroxy-4,4'-dimethoxy-2-hydroxybenzophenone, and compounds of formula:

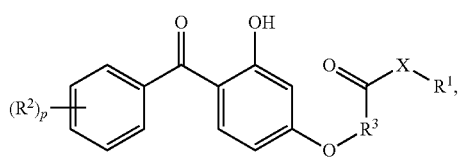

wherein
X is NH or O;
R¹ is H or [C₂-C₄-alkoxy]ₙ-(C₁-C₁₈-alkyl) or —[CH₂CH₂NH]ₙ—H;
R² is OH or C₁-C₈-alkoxy;
p is an integer between 0 and 5; and
R³ is H or C₁-C₈-alkyl; and
n is an integer between 3 and 50;
G) sulfonic acid derivatives of benzophenones selected from 2-hydroxy-4-methoxybenzophenone-5-sulfonic acid and its salts, and 2,2'-dihydroxy-4,4'-dimethoxybenzophenone-5,5'-sulfonic acid and its salts;
H) 3-benzylidenecamphor and derivatives thereof selected from 3-(4'-methylbenzyl-idene)d-1-camphor, and benzylidiene camphor sulfonic acid;
I) sulfonic acid derivatives of 3-benzylidenecamphor selected from 4-(2-oxo-3-bor-nylidenemethyl)benzenesulfonic acid and 2-methyl-5-(2-oxo-3-bornyl-idene) sulfonic acid and salts thereof;
J) esters of benzalmalonic acid selected from 2-ethylhexyl 4-methoxybenzmalonate;
K) triazine derivatives selected from dioctylbutamidotriazone, 2,4,6-trinanilino-p-(carbo-2'-ethyl-hexyl-1'-oxy)-1,3,5-triazine, 2-[4-[(2-Hydroxy-3-(2'-ethyl)hexyl)oxy]-2-hydroxyphenyl]-4,6bis(2,4-dimethylphenyl)-1,3,5-triazine, anisotriazine, 2,4,6-tris(diisobutyl 4'-aminobenzalmalonate)-s-triazine, and compounds of formula

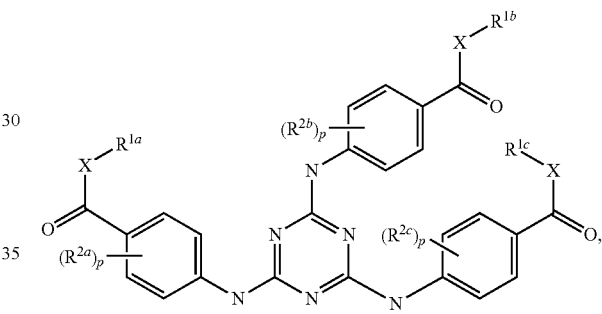

wherein
X is NH or O;
R¹ᵃ, R¹ᵇ, R¹ᶜ are independently of each other H, [C₂-C₄-alkoxy]ₙ-(C₁-C₁₈-alkyl) or —[CH₂CH₂NH]ₙ—H;
R²ᵃ, R²ᵇ, R²ᶜ are independently of each other OH or C₁-C₈-alkoxy;
p is an integer between 0 and 4; and
n is an integer between 3 and 50;
L) propane-1,3-diones selected from 1-(4-tert-butylphenyl)-3-(4'-methoxyphenyl)propane-1,3-dione;
M) 2-phenylbenzimidazole-5-sulfonic acid or 2-phenylbenzimidazole-4-sulfonic acid and alkali metal, alkaline earth metal, ammonium, alkylammonium, alkanolammonium or glucammonium salts thereof;
N) derivatives of benzoylmethane selected from 1-(4'-tert-butylphenyl)-3-(4'-methoxy-phenyl)propane-1,3-dione, 4-tert-butyl-4'-methoxydibenzoylmethane and 1-phenyl-3-(4'-isopropylphenyl)propane-1,3-dione;
O) aminohydroxy-substituted derivatives of benzophenones selected from N,N-diethylaminohydroxybenzoyl-n-hexylbenzoate; and
P) a mixture of p-methoxycinnamic acid ethylhexyl ester (65%) and 2-(4-diethylamino-2-hydroxybenzoyl)benzoic acid hexylester (35%).

2. The method according to claim 1 for reducing light-dependent symptoms caused by excessive sunlight wherein said symptoms comprise wilting, chloroses, necroses, and/or spotting of the aerial parts.

3. The method according to claim 1, wherein the UV filter is water-soluble.

4. The method according to claim 3, wherein the UV filter is selected from group A).

5. The method according to claim 1, wherein the crop plant is barley and a symptom to be reduced is physiological leafspots.

6. The method according to claim 1, wherein the composition comprises a mixture of at least one UV filter and at least one active substance selected from the group consisting of:
A') strobilurins,
B') carboxamides selected from
  carboxanilides,
  carboxylic morpholides,
  benzoic acid amides,
  carpropamid, dicyclomet, mandiproamid, oxytetracyclin, silthiofarm and N-(6-methoxy-pyridin-3-yl)cyclopropanecarboxylic acid amide,
C') azoles selected from
  triazoles,
  imidazoles,
  benzimidazoles, and
  ethaboxam, etridiazole, hymexazole and 2-(4-chlorophenyl)-N-[4-(3,4-dimethoxy-phenyl)-isoxazol-5-yl]-2-prop-2-ynyloxy-acetamide,
D') heterocyclic compounds selected from
  pyridines
  pyrimidines
  piperazines
  pyrroles
  morpholines
  piperidines
  dicarboximides
  non-aromatic 5-membered heterocycles; and
  acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, and 5-chloro-7-(4-methylpiperidin-1-yl)-6-(2,4,6-trifluorophenyl)-[1,2,4]triazolo-[1,5-a]pyrimidine and 5-ethyl-6-octyl-[1,2,4]triazolo[1,5-a]pyrimidine-7-ylamine,
E') carbamates selected from
  thio- and dithiocarbamates
F') other active substances selected from
  guanidines,
  antibiotics,
  nitrophenyl derivates,
  organometal compounds,
  sulfur-containing heterocyclyl compounds,
  organophosphorus compounds,
  organochlorine compounds,
  inorganic active substances,
  biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester; and
G') inorganic substances selected from
  kaolin and metal oxides.

7. The method according to claim 6, wherein the at least one active substance is selected from the group consisting of:
A') strobilurins selected from
  azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl(2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;
B') carboxanilides selected from: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide;
carboxylic morpholides selected from: dimethomorph, flumorph, pyrimorph;
benzoic acid amides selected from: flumetover, fluopicolide, fluopyram, zoxamide, N-(3-Ethyl-3,5,5-trimethyl-cyclohexyl)-3-formylamino-2-hydroxy-benzamide;
carpropamid, dicyclomet, mandiproamid, oxytetracyclin, silthiofarm and N-(6-methoxy-pyridin-3-yl)cyclopropanecarboxylic acid amide;
C') triazoles selected from: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, and 1-(4-chloro-phenyl)-2-([1,2,4]triazol-1-yl)-cycloheptanol;
imidazoles selected from: cyazofamid, imazalil, pefurazoate, prochloraz, and triflumizol;
benzimidazoles selected from: benomyl, carbendazim, fuberidazole, and thiabendazole; and
ethaboxam, etridiazole, hymexazole and 2-(4-chloro-phenyl)-N-[(3,4-dimethoxy-phenyl)-isoxazol-5-yl]-2-prop-2-ynyloxy-acetamide;
D') pyridines selected from: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, and N-(1-(5-bromo-3-chloro-pyridin-2-yl)-ethyl)-2,4-dichloronicotinamide, and N-[(5-bromo-3-chloro-pyridin-2-yl)-methyl]-2,4-dichloronicotinamide;

pyrimidines selected from: bupirimate, cyprodinil, diflumetorim, fenarimol, ferimzone, mepanipyrim, nitrapyrin, nuarimol, and pyrimethanil;

piperazines selected from: triforine;

pyrroles selected from: fenpiclonil, and fludioxonil;

morpholines selected from: aldimorph, dodemorph, dodemorph-acetate, fenpropimorph, and tridemorph;

piperidines selected from: fenpropidin;

dicarboximides selected from: fluoroimid, iprodione, procymidone, and vinclozolin;

non-aromatic 5-membered heterocycles selected from: famoxadone, fenamidone, flutianil, octhilinone, probenazole, and 5-amino-2-isopropyl-3-oxo-4-ortho-tolyl-2,3-dihydro-pyrazole-1-carbothioic acid S-allyl ester;

acibenzolar-S-methyl, amisulbrom, anilazin, blasticidin-S, captafol, captan, chinomethionat, dazomet, debacarb, diclomezine, difenzoquat, difenzoquat-methyl-sulfate, fenoxanil, Folpet, oxolinic acid, piperalin, proquinazid, pyroquilon, quinoxyfen, triazoxide, tricyclazole, 2-butoxy-6-iodo-3-propylchromen-4-one, and 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo-[1,5-a]pyrimidine and 5-ethyl-6-octyl-[1,2,4]triazolo[1,5-a]pyrimidine-7-ylamine;

E') thio- and dithiocarbamates selected from: ferbam, mancozeb, maneb, metam, methasulphocarb, metiram, propineb, thiram, zineb, ziram;

carbamates selected from: benthiavalicarb, diethofencarb, iprovalicarb, propamocarb, propamocarb hydrochlorid, valiphenal and N-(1-(1-(4-cyano-phenyl)ethanesulfonyl)-but-2-yl) carbamic acid-(4-fluorophenyl) ester; and F') guanidines selected from: guanidine, dodine, dodine free base, guazatine, guazatine-acetate, iminoctadine, iminoctadine-triacetate, and iminoctadine-tris(albesilate);

antibiotics selected from: kasugamycin, kasugamycin hydrochloride-hydrate, streptomycin, polyoxine, validamycin A;

nitrophenyl derivates selected from: binapacryl, dinobuton, dinocap, nitrthal-isopropyl, and tecnazen, organometal compounds selected from: fentin salts selected from fentin-acetate, fentin chloride and fentin hydroxide;

sulfur-containing heterocyclyl compounds selected from: dithianon, and isoprothiolane;

organophosphorus compounds selected from: edifenphos, fosetyl, fosetyl-aluminum, iprobenfos, phosphorous acid and its salts, pyrazophos, and tolclofos-methyl;

organochlorine compounds selected from: chlorothalonil, dichlofluanid, dichlorophen, flusulfamide, hexachlorobenzene, pencycuron, pentachlorphenole and its salts, phthalide, quintozene, thiophanate-methyl, tolylfluanid, and N-(4-chloro-2-nitro-phenyl)-N-ethyl-4-methyl-benzenesulfonamide;

inorganic active substances selected from: Bordeaux mixture, copper acetate, copper hydroxide, copper oxychloride, basic copper sulfate, and sulfur; and biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester; and G') kaolin and metal oxides selected from $TiO_2$, $ZnO$ and $CeO_2$.

* * * * *